United States Patent
Manley et al.

(10) Patent No.: US 9,636,131 B2
(45) Date of Patent: May 2, 2017

(54) SURGICAL TOOL ARRANGEMENT AND SURGICAL CUTTING ACCESSORY FOR USE THEREWITH

(71) Applicants: Kevin Manley, Cobh (IE); Brian Fouts, San Martin, CA (US); Bryan G. Deeny, Douglas (IE); James M. Hayes, San Jose, CA (US)

(72) Inventors: Kevin Manley, Cobh (IE); Brian Fouts, San Martin, CA (US); Bryan G. Deeny, Douglas (IE); James M. Hayes, San Jose, CA (US)

(73) Assignee: STRYKER CORPORATION, Kalamazoo, MI (US)

( * ) Notice: Subject to any disclaimer, the term of this patent is extended or adjusted under 35 U.S.C. 154(b) by 392 days.

(21) Appl. No.: 14/190,185

(22) Filed: Feb. 26, 2014

(65) Prior Publication Data
US 2014/0277041 A1 Sep. 18, 2014

Related U.S. Application Data

(60) Provisional application No. 61/791,527, filed on Mar. 15, 2013.

(51) Int. Cl.
A61B 17/32 (2006.01)
A61B 17/16 (2006.01)

(52) U.S. Cl.
CPC .... *A61B 17/32002* (2013.01); *A61B 17/1615* (2013.01); *A61B 2217/005* (2013.01)

(58) Field of Classification Search
CPC ........... A61B 17/1613–17/1617; A61B 17/320016–17/32002; A61B 17/3207; A61B 17/320758; A61B 17/320783; A61B 2017/320024–2017/32004; A61B 2017/320766–2017/320791
USPC ................ 606/159, 167, 170–172
See application file for complete search history.

(56) References Cited

U.S. PATENT DOCUMENTS

| | | | |
|---|---|---|---|
| 3,732,858 A | 5/1973 | Banko | |
| 3,844,272 A | 10/1974 | Banko | |
| 4,030,503 A * | 6/1977 | Clark, III | A61B 17/3207 606/159 |
| 4,445,509 A | 5/1984 | Auth | |
| 4,646,738 A | 3/1987 | Trott | |
| 4,842,578 A | 6/1989 | Johnson et al. | |
| 4,867,157 A | 9/1989 | McGurk-Burleson et al. | |

(Continued)

FOREIGN PATENT DOCUMENTS

| | | |
|---|---|---|
| AU | 3781400 A | 7/2000 |
| CA | 2 398 850 A1 | 8/2001 |

(Continued)

OTHER PUBLICATIONS

"The Formula For Success" brochure dated 2007 (6 pages).

*Primary Examiner* — Victor Nguyen
*Assistant Examiner* — Jonathan Hollm
(74) *Attorney, Agent, or Firm* — Flynn, Thiel, Boutell & Tanis, P.C.

(57) ABSTRACT

A surgical tool arrangement for performing endoscopic surgical procedures which includes a powered handpiece and a cutting accessory which detachably connects to the handpiece. The cutting accessory has a distal end which defines a cutting head incorporating a suction arrangement directly adjacent the cutting features thereof.

14 Claims, 12 Drawing Sheets

(56) References Cited

U.S. PATENT DOCUMENTS

| | | | |
|---|---|---|---|
| 4,983,179 A | 1/1991 | Sjostrom | |
| 5,084,052 A | 1/1992 | Jacobs | |
| 5,217,479 A | 6/1993 | Shuler | |
| 5,269,798 A | 12/1993 | Winkler | |
| 5,366,468 A | 11/1994 | Fucci et al. | |
| 5,489,291 A | 2/1996 | Wiley | |
| 5,492,527 A | 2/1996 | Glowa et al. | |
| 5,592,727 A | 1/1997 | Glowa et al. | |
| 5,601,583 A | 2/1997 | Donahue et al. | |
| 5,620,447 A | 4/1997 | Smith et al. | |
| 5,693,063 A | 12/1997 | Van Wyk et al. | |
| 5,759,185 A * | 6/1998 | Grinberg | A61B 17/1615 606/180 |
| 5,766,199 A | 6/1998 | Heisler et al. | |
| 5,833,692 A | 11/1998 | Cesarini et al. | |
| 5,833,702 A | 11/1998 | Van Wyk et al. | |
| 5,843,106 A | 12/1998 | Heisler | |
| 5,851,208 A | 12/1998 | Trott | |
| 5,913,867 A | 6/1999 | Dion | |
| 6,001,116 A | 12/1999 | Heisler et al. | |
| 6,053,923 A | 4/2000 | Veca et al. | |
| 6,053,928 A | 4/2000 | Van Wyk et al. | |
| 6,068,641 A | 5/2000 | Varsseveld | |
| 6,183,487 B1 * | 2/2001 | Barry | A61B 17/32075 606/159 |
| 6,217,598 B1 | 4/2001 | Berman et al. | |
| 6,312,438 B1 | 11/2001 | Adams | |
| 6,312,441 B1 | 11/2001 | Deng | |
| 6,620,180 B1 | 9/2003 | Bays et al. | |
| 6,827,725 B2 | 12/2004 | Batchelor et al. | |
| 7,077,845 B2 | 7/2006 | Hacker et al. | |
| 7,237,990 B2 | 7/2007 | Deng | |
| 7,618,428 B2 | 11/2009 | O'Quinn et al. | |
| 7,682,333 B2 | 3/2010 | Deng | |
| 7,803,170 B2 | 9/2010 | Mitusina | |
| 7,887,559 B2 | 2/2011 | Deng et al. | |
| 8,062,319 B2 | 11/2011 | O'Quinn et al. | |
| 2002/0029055 A1 * | 3/2002 | Bonutti | A61B 10/025 606/170 |
| 2003/0135151 A1 | 7/2003 | Deng | |
| 2004/0092991 A1 | 5/2004 | Deng | |
| 2004/0220602 A1 | 11/2004 | Deng et al. | |
| 2005/0065538 A1 | 3/2005 | Van Wyk | |
| 2006/0142775 A1 | 6/2006 | Heneberry et al. | |
| 2006/0196038 A1 | 9/2006 | Van Wyk | |
| 2006/0212060 A1 | 9/2006 | Hacker et al. | |
| 2008/0208194 A1 | 8/2008 | Bickenbach | |
| 2010/0298855 A1 | 11/2010 | Dierck | |
| 2011/0238099 A1 | 9/2011 | Loreth | |
| 2012/0150209 A1 | 6/2012 | Gubellini et al. | |
| 2012/0203230 A1 | 8/2012 | Adams | |
| 2013/0274779 A1 | 10/2013 | Kulas et al. | |

FOREIGN PATENT DOCUMENTS

| | | |
|---|---|---|
| CA | 2 361 354 A1 | 5/2002 |
| DE | 697 32 580 T2 | 5/2006 |
| EP | 0 796 064 A1 | 9/1997 |
| EP | 0 800 793 A1 | 10/1997 |
| EP | 0 836 833 A2 | 4/1998 |
| EP | 1 006 898 B1 | 6/2000 |
| EP | 1 253 863 B1 | 11/2002 |
| EP | 1 676 537 A1 | 7/2006 |
| EP | 1 702 573 A1 | 9/2006 |
| EP | 2 470 085 A1 | 7/2012 |
| EP | 2 484 297 A1 | 8/2012 |
| GB | 2 093 353 A | 9/1982 |
| WO | WO 92/15255 A1 | 9/1992 |
| WO | WO 98/27876 A1 | 7/1998 |
| WO | WO 00/78236 A1 | 12/2000 |
| WO | WO 01/05313 A1 | 1/2001 |
| WO | WO 2006/102124 A2 | 9/2006 |
| WO | WO 2013/158469 A1 | 10/2013 |

* cited by examiner

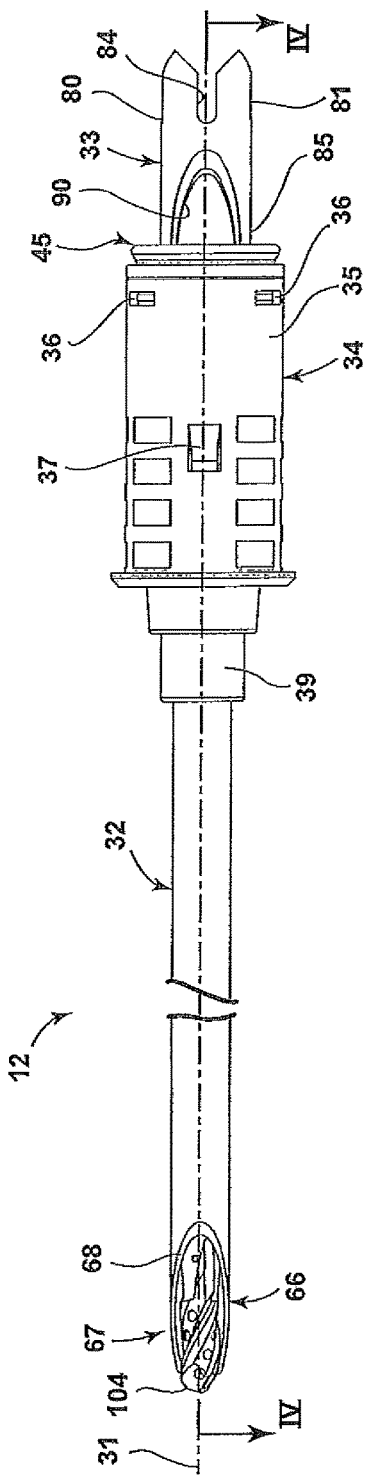
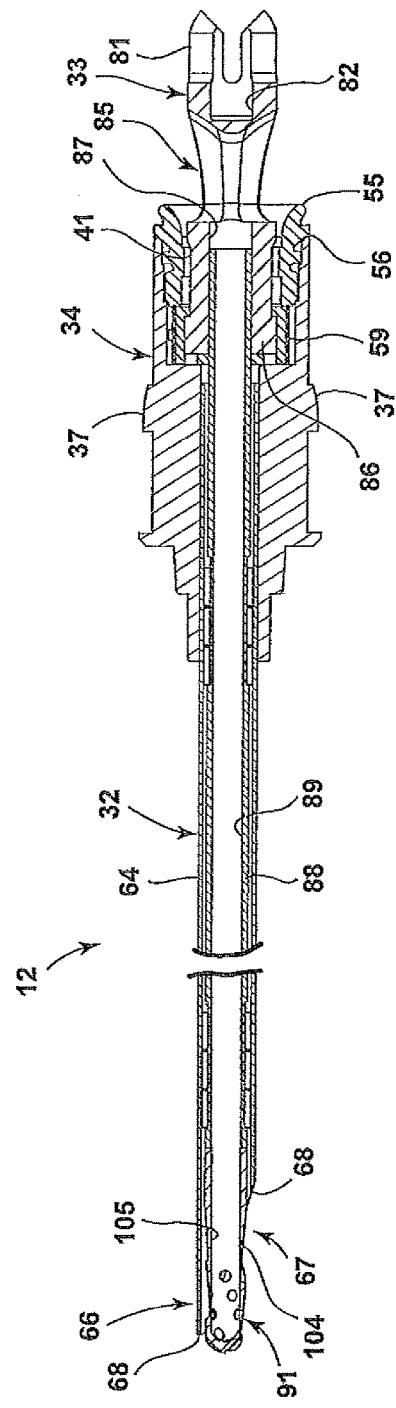
FIG. 3
FIG. 4

SURGICAL TOOL ARRANGEMENT AND SURGICAL CUTTING ACCESSORY FOR USE THEREWITH

CROSS REFERENCE TO RELATED APPLICATION

This application claims the benefit of U.S. Provisional Application Ser. No. 61/791,527, filed Mar. 15, 2013, which is incorporated herein by reference in its entirety.

FIELD OF THE INVENTION

This invention generally relates to a surgical tool arrangement useful for performing endoscopic surgical procedures which includes a powered handpiece and, more particularly, to a cutting accessory which detachably connects to the handpiece and incorporates a suction arrangement at the distal end of the cutting accessory directly adjacent the cutting features thereof.

BACKGROUND OF THE INVENTION

Endoscopic surgical procedures are routinely performed in order to accomplish various surgical tasks. In such a surgical procedure, small incisions or portals are made in the patient. An endoscope, which is a device that allows medical personnel to view the surgical site, is inserted in one of the portals. Surgical instruments used to perform other tasks are inserted into other portals. The surgeon views the surgical site through the endoscope to determine how to manipulate the surgical instruments in order to accomplish the desired procedure. An advantage of performing endoscopic surgery is that, since the portions of the body that are cut open are minimized, the portions of the body that need to heal after the surgery are likewise reduced. Moreover, during an endoscopic surgical procedure, only relatively small portions of the patient's internal organs and tissue are exposed to the open environment. This minimal opening of the patient's body lessens the extent to which the organs and tissue are open to infection.

The ability to perform endoscopic surgery is enhanced by the development of powered surgical tools especially designed to perform such procedures. Once such tool is sold by the assignee hereof under the trademark FORMULA®. This tool is in the form of a cylindrical handpiece designed to be held in the hand of the surgeon. The handpiece has a front or distal end provided with a coupling assembly for releasably holding a cutting accessory, and a motor disposed within a handpiece housing which drives the accessory. The cutting accessories, such as shavers, drills and burs, include a hub which defines the proximal end of the accessory and is appropriately configured to cooperate with the coupling assembly of the handpiece to lock the accessory thereto, an elongated and tubular housing element having a proximal end fixed to the hub, and an elongated cutting element including a drive shaft disposed within the housing element. When the accessory is attached to the handpiece, the handpiece motor couples to the drive shaft of the accessory and moves same relative to the outer housing element. The handpiece motor is selectively actuable to drive the accessory drive shaft so as to cause a desired cutting action at the distal end of the accessory. The handpiece is associated with a control unit which controls the functioning thereof, and is actuated by the user via appropriate buttons provided on the handpiece itself, at the control unit or through use of a footswitch.

In an endoscopic surgical procedure, irrigating fluid is introduced into the surgical site. This fluid serves as a transport media for removing tissue and debris from the surgical site. In order to remove the irrigating fluid and the material contained therein, the above handpiece and the various accessories which are usable therewith together define a suction conduit. A suction pump is connected to the handpiece to provide the suction force needed for drawing the fluid and material away from the surgical site. In order to control the suction flow through the accessory and the handpiece, the handpiece is typically provided with a manually operated valve which is manipulated by the surgeon to control suction of material away from the surgical site.

Mechanical cutting accessories, such as the shaver, drill and bur discussed above, are commonly used in arthroscopic procedures, and allow for the resection of hard and soft bodily tissues, for example, those found within the knee, shoulder and other joints. A bur-type cutting accessory is commonly used to resect bone or other hard tissues, and includes cutting features which when rotated serve to cut away targeted bone or hard tissue. Such cutting features may be helically-oriented or non-helically oriented. The cutting element of a bur-type cutting accessory includes a cutting head with these cutting features which are exposed through a window formed at the distal end of the outer housing element when the cutting element is located therein. In some bur-type cutting accessories, the window formed in the outer housing element opens primarily sidewardly, so that the distal end of the outer housing element covers a portion or one side of the cutting head of the bur to allow the user to better target bone or hard tissue. Alternatively, the entire cutting head geometry may project distally beyond the terminal end of the outer housing element, and this type of bur configuration is often called "unhooded". Many bur configurations are for removal of particular bone or hard tissue types, and a variety of different bur geometries are available to specifically address the type of cutting the accessory is to carry out.

Further, in some conventional bur-type cutting accessories, the cutting element includes an elongate and hollow tubular drive shaft and the cutting head at the distal end thereof is provided as a solid member which is fixedly mounted to the distal end of the drive shaft. In order to draw suction through the cutting element in this type of accessory, the distal end of the drive shaft is provided with a suction opening which opens sidewardly outwardly and communicates with the hollow interior of the drive shaft. In operation, bone or other hard tissue removed or cut away by the cutting head is suctioned into the hollow interior of the drive shaft through the window of the outer housing element. Bur-type cutting accessories, due to their configuration, often spray surgical debris outwardly and away from the cutting features of the cutting head. Eventually, the surgical debris will be evacuated from the surgical site through the suction opening located proximally from the cutting head of the bur. However, in the interim, the debris can occlude the surgeon's field of view.

The cutting accessory disclosed in U.S. Pat. No. 5,489,291 includes an abrading element which is generally hollow and includes a plurality of helically-oriented apertures, each of which apertures is disposed between an adjacent pair of abrading ridges. These helically-oriented apertures provide a path for fluid and abraded tissue into the central bore of the tool. However, the configuration of the abrading element is primarily hollow, and the suction apertures are elongate and extend a substantial longitudinal distance along the abrading element, and such an open configuration compromises the structural integrity of the abrading element. Further, the suction apertures and the abrading ridges are formed together or at the same time, which necessarily limits the design flexibility of both the abrading ridges and the suction apertures.

While the arrangements described above serve to remove fluid and surgical debris from the surgical site, there is a continuing desire and need for improved performance in surgical tools in an effort to minimize trauma to the patient and to make the operative procedure more efficient and effective. The surgical accessory according to the invention includes a cutting element with a cutting head which incorporates one or more suction openings directly adjacent the cutting features of the cutting head. In one embodiment, the cutting head has a generally helically oriented cutting edge, and a suction opening or alternatively a plurality of openings in communication with a source of suction, are located directly adjacent the cutting edge. Another embodiment of the invention includes a cutting head with a cutting edge and a suction opening which traverses the cutting edge. A further embodiment of the invention includes a cutting head with a cutting edge which is generally straight or linear and a suction opening or a plurality of suction openings disposed directly adjacent the cutting edge.

The placement of the suction opening or openings according to the invention serves to evacuate surgical debris from the surgical site rapidly after the debris is generated and thus results in a much reduced delay between the time debris is generated and the time the debris is evacuated from the surgical site, thereby preventing or at least minimizing any occlusion of the surgeon's field of view and providing an overall clearer field of view during use of the accessory. Additionally, the size, placement and process for forming the suction openings allow for a cutting element with increased structural integrity. Further, the suction opening or openings provided in the cutting head in some embodiments are formed in a cutting step which is separate from the cutting step during which the cutting edges or features are formed. Thus, the suction opening or openings can be oriented and/or the size thereof modified without modifying the trajectory and/or configuration of the cutting features.

BRIEF DESCRIPTION OF THE DRAWINGS

FIG. 3 is an enlarged top and fragmentary view of the surgical accessory;

FIG. 4 is an enlarged longitudinal cross-sectional view of the surgical accessory of FIG. 3, as seen generally along line IV-IV in FIG. 3;

Figure 1:
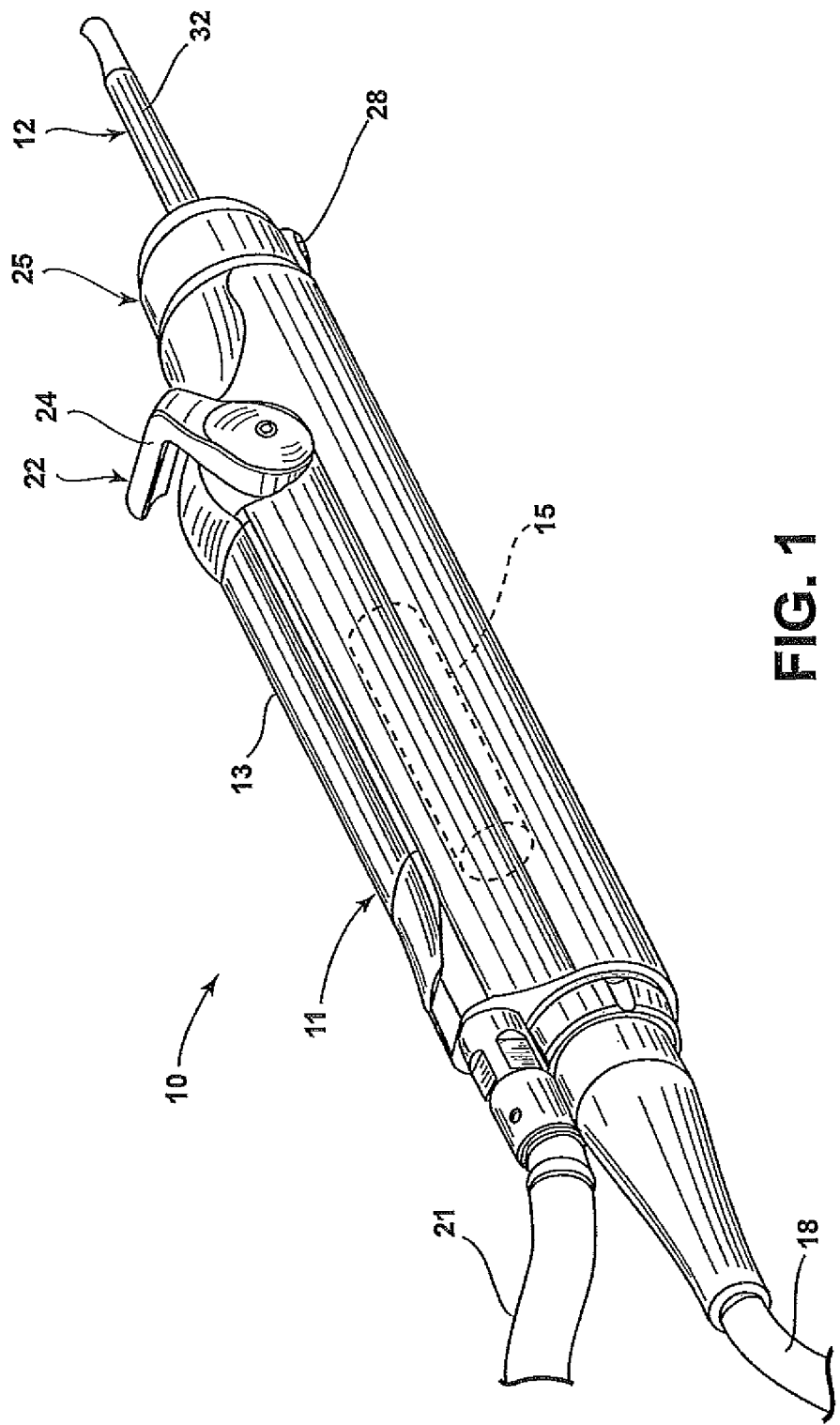
FIG. 1 is a perspective view of the surgical tool arrangement according to the invention, including a handpiece with a surgical accessory attached thereto.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement and designated parts thereof. The words "forwardly" and "distally" will refer to the direction toward the end of the arrangement which is closest to the patient, and the words "rearwardly" and "proximally" will refer to the direction toward the end of the arrangement which is furthest from the patient. Said terminology will include the words specifically mentioned, derivatives thereof, and words of similar import.

DETAILED DESCRIPTION

Figure 2:
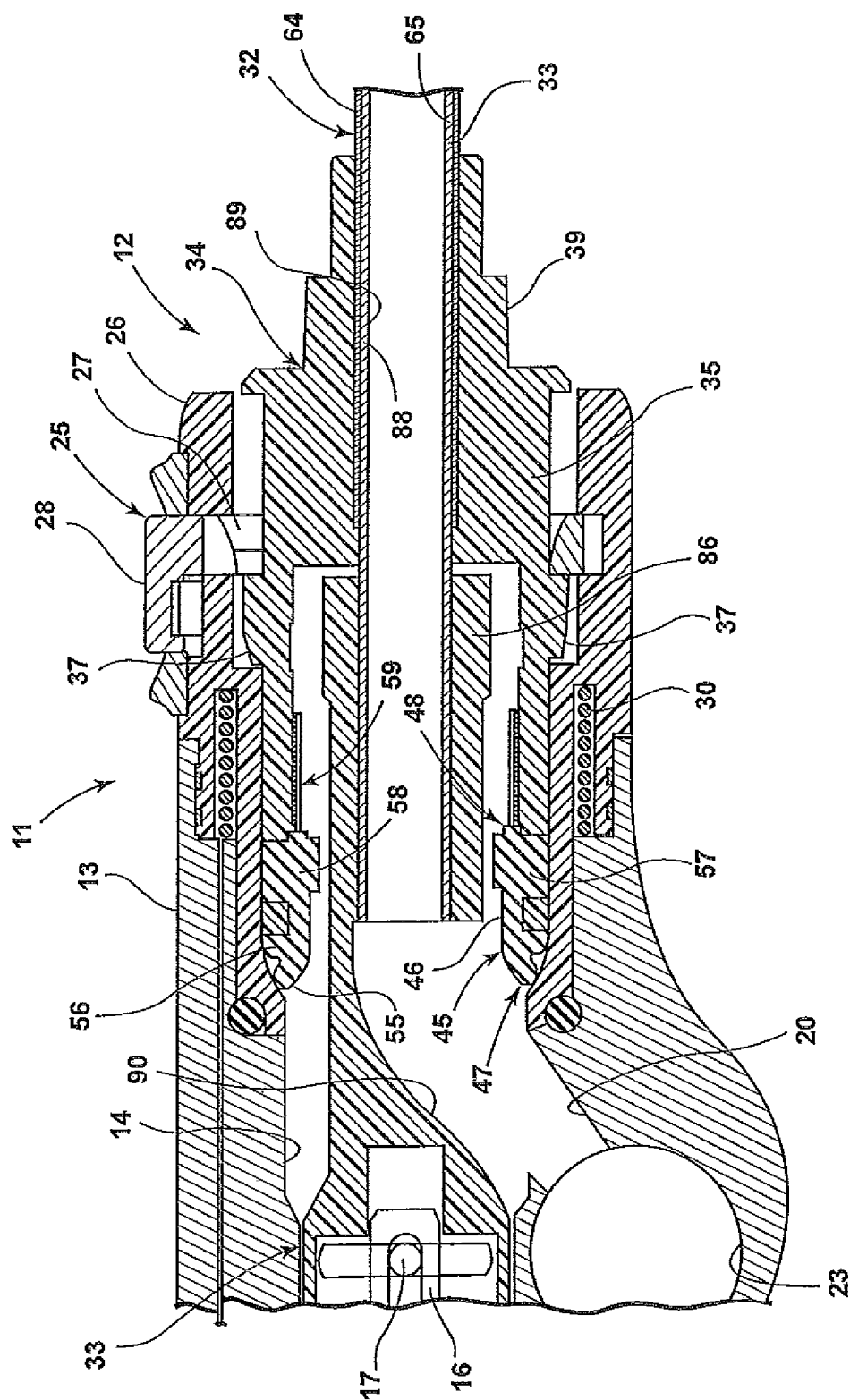
FIG. 2 is an enlarged, fragmentary, longitudinal and cross-sectional view of the handpiece of FIG. 1 with a surgical accessory attached thereto.
Figure 5:
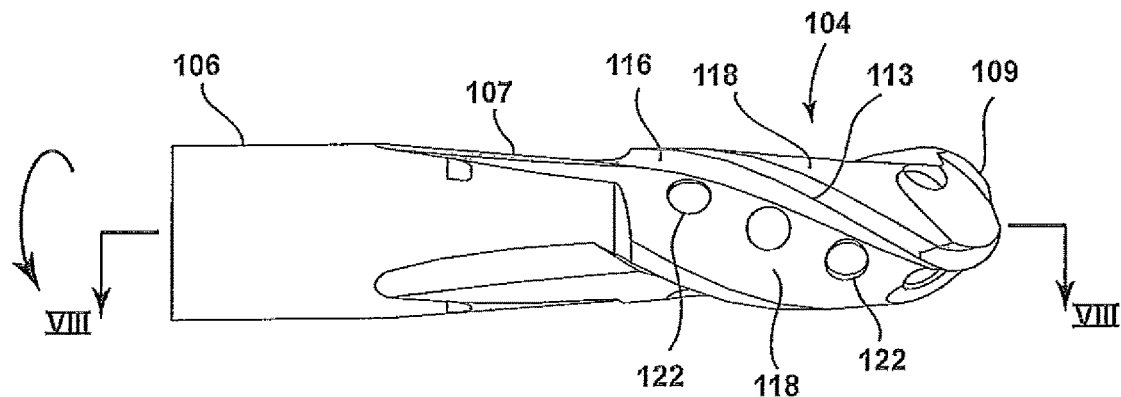
FIG. 5 is an enlarged and isolated side view of a first embodiment of the cutting head of the surgical accessory.
Figure 6:
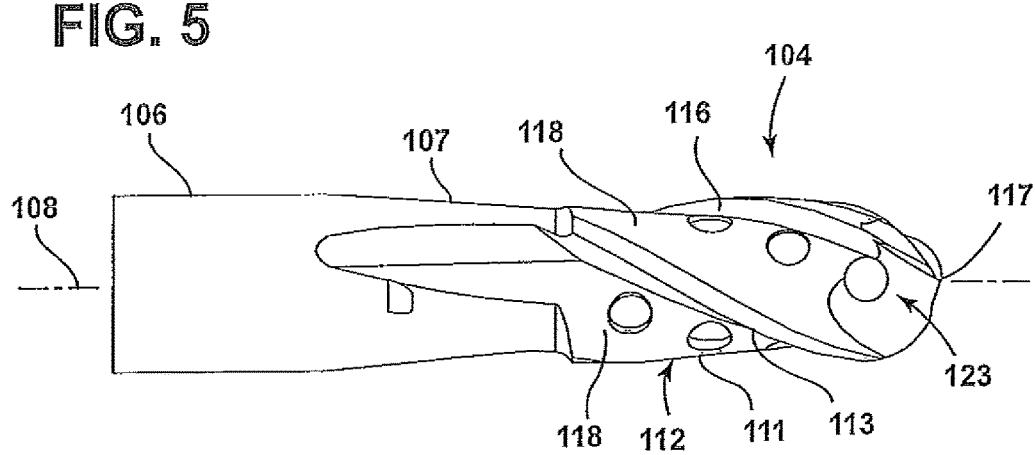
FIG. 6 is an enlarged and isolated side view of the first embodiment of the cutting head of the surgical accessory rotated approximately 180 degrees from the position shown in FIG. 5.
Figure 7:
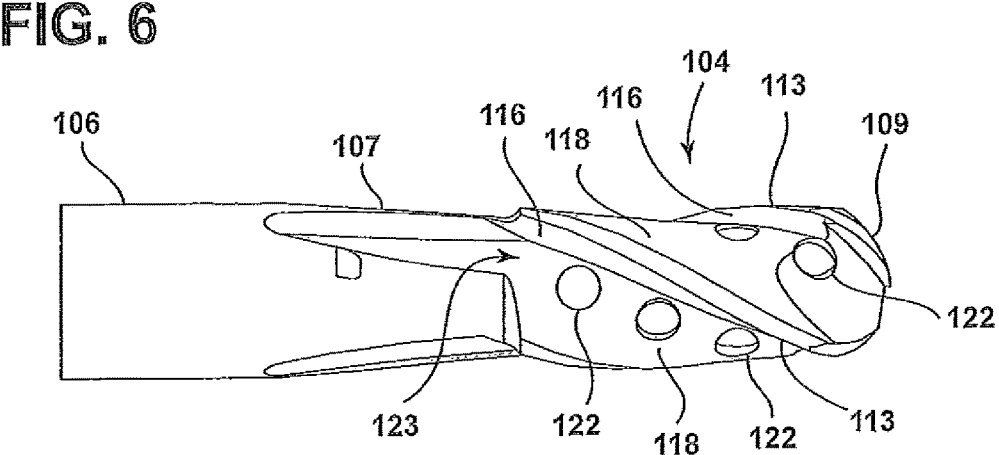
FIG. 7 is an enlarged and isolated side view of the first embodiment of the cutting head of the surgical accessory rotated approximately 90 degrees towards the viewer from the position shown in FIG. 6.

Referring to FIGS. 1 and 2, a surgical tool arrangement 10 according to the invention is illustrated. The arrangement 10 includes a handpiece 11, which at its distal end mounts thereon a surgical accessory 12.

Handpiece 11 is a commercially available surgical handpiece manufactured by the assignee hereof, under Model Nos. 375-704-500 and 375-701-500, and is accordingly only briefly described herein. Handpiece 11 includes an elongate outer housing 13 defining an elongate bore 14 therein. A motor 15 (shown diagrammatically only in FIG. 1) is disposed within housing bore 14. Motor 15 includes an output or drive shaft 16, which drive shaft 16 mounts a drive pin 17 at the distal end thereof. A power cable 18 is coupled to the proximal end of handpiece 11 for supplying power to motor 15.

Handpiece housing 13 defines therein an elongate suction bore (not shown) extending generally parallel to and sidewardly of housing bore 14. This suction bore communicates with a diagonally extending suction passage 20 defined in housing 13, which passage 20 provides communication between the distal end of housing bore 14 and the suction bore. Suction is drawn through the handpiece 11 by a suction pump (not shown), which is connected to the handpiece 11 via a suction tube 21. Suction flow through the handpiece 11 is regulated by an adjustable valve 22 having a valve stem (not shown) which is movably mounted in a valve bore 23 defined in housing 13. The valve 22 is adjusted by the user via a movable handle or arm 24 connected to the valve stem. The above handpiece suction arrangement is described in detail in U.S. Pat. No. 7,682,333 issued on Mar. 23, 2010, which patent is owned by the same assignee hereof and is hereby incorporated by reference herein in its entirety.

The accessory 12 is removably attached to the distal end of the handpiece 11 by a coupling assembly 25 provided on the handpiece 11. Coupling assembly 25 includes a generally ring-shaped collet 26 secured to the distal end of the handpiece housing 13. A locking ring 27 is movably disposed in collet 26 and is biased to hold the accessory 12 within the housing bore 14 of handpiece 11. A release button 28 is provided on locking ring 27, and is used to release the locking ring 27 and allow removal of the accessory 12 from handpiece 11. Further, a coil 30 is provided in collet 26, which is used to facilitate inductive signal transfer to/from a radio-frequency identification device (RFID) disposed in the accessory 12 as discussed below.

Referring to FIGS. 2-4, the accessory 12 will now be described. Accessory 12 defines a central longitudinal axis 31, and includes an outer cannula or tubular housing element 32 and a tubular cutting element 33 disposed within housing element 32. Housing element 32 includes a hub 34 which defines the proximal end thereof. Hub 34 is defined by a generally tubular base body 35, which defines therein a pair of generally rectangular and diametrically-opposed openings 36 adjacent the proximal end thereof. Base body 35 also has formed thereon a pair of outwardly-projecting, diametrically opposed and generally ramp-shaped ears 37 disposed distally of openings 36. Ears 37 cooperate with coupling assembly 25 of handpiece 11 to secure accessory 12 therein. Hub 34 has a distal end defined by a head 39 or nose of a reduced diameter as compared to base body 35. Further, hub 34 defines therein a bore 41 which extends completely through the hub 34, and with which openings 36 of base body 35 communicate.

An annular seal 45 is disposed within the proximal end of bore 41 of hub 34. Seal 45 is constructed of a resilient elastomeric material, and is defined by a main section 46 and axially-spaced proximal and distal sections 47 and 48 disposed at respective opposite ends of the main section 46. Proximal section 47 defines thereon a pair of annular ribs 55 and 56, which are disposed in sealing engagement with an inner annular surface of collet 26 of handpiece 11 when accessory 12 is coupled thereto, as shown in FIG. 2. Distal section 48 defines thereon a pair of outwardly projecting and diametrically-opposed lock tabs 57 which engage within the respective openings 36 of hub 34 to secure the seal 45 to hub 34 and fix the axial position of seal 45 relative thereto. Distal section 48 additionally defines thereon a pair of inwardly projecting and diametrically-opposed stop tabs 58, which are generally radially aligned with the respective lock tabs 57. As shown in FIGS. 2 and 4, an RFID device 59 encapsulated within a ring structure is located within hub bore 41 distally from, and in axially-adjacent relationship with, the distal section 48 of seal 45.

The above-described coupling arrangement of handpiece 11 and the arrangement of the encapsulated RFID device 59 and coil 30 are disclosed in U.S. Pat. No. 7,887,559 issued on Feb. 15, 2011, which patent is owned by the same assignee hereof and is hereby incorporated by reference herein in its entirety.

Housing element 32 additionally includes an elongate housing tube 64 which projects distally from hub 34. More specifically, housing tube 64 has a proximal end which is fixedly mounted within the distal portion of bore 41 of hub 34. Housing tube 64 defines an elongate bore or conduit 65 therein, in which the cutting element 33 is disposed as discussed below. Referring to FIGS. 3 and 4, housing tube 64 has a distal end 66 which in the illustrated embodiment is cut so as to define a window 67 having an annular edge 68, which window 67 in the illustrated embodiment opens both sidewardly and distally of the tube 64. Alternatively, the distal end 66 of housing tube 64 may be cut in a manner such that annular edge 68 is oriented perpendicular to the axis 31. Other configurations of distal end 66 of housing tube 64 are within the scope of the invention, and the above are given only by way of example.

Turning now to cutting element 33, same includes a hub 80 which defines the proximal end thereof. Hub 80 incorporates a motor-engaging drive element 81 defining a proximally opening bore 82, and a slot 84 which extends transversely to the longitudinal axis of the cutting element 33. Hub 80 additionally includes a neck 85 which projects distally from drive element 81. Neck 85 terminates at a head 86 which has an enlarged outer diameter. In this regard, the outer diameter of head 86 is slightly larger than the inward projection of the respective stop tabs 58 of seal 45. A bore 87 extends through neck 85 and head 86, in which an elongate and tubular drive shaft 88 is fixed. Drive shaft 88 defines therein a suction passage 89 which is in communication with a suction port 90 defined in neck 85, which suction port 90 is in turn in communication with suction passage 20 of handpiece 11.

Drive shaft 88 has a distal end 91 which mounts a cutting head 104 thereon. In the illustrated embodiment, the drive shaft 88 and the cutting head 104 are constructed as separate components which are fixed to one another. In this regard, the drive shaft 88 may be constructed of a rigid plastic and then induction welded to the cutting head 104, which may be constructed of rigid metal, such as stainless steel. Alternatively, the drive shaft 88 and the cutting head 104 may be constructed as an integral or one-piece member formed from rigid metal, such as stainless steel. The cutting head 104 is generally cylindrical and tubular in the illustrated embodiment, and defines a hollow interior 105 which extends along substantially the entire longitudinal extent of cutting head 104.

Figure 8:
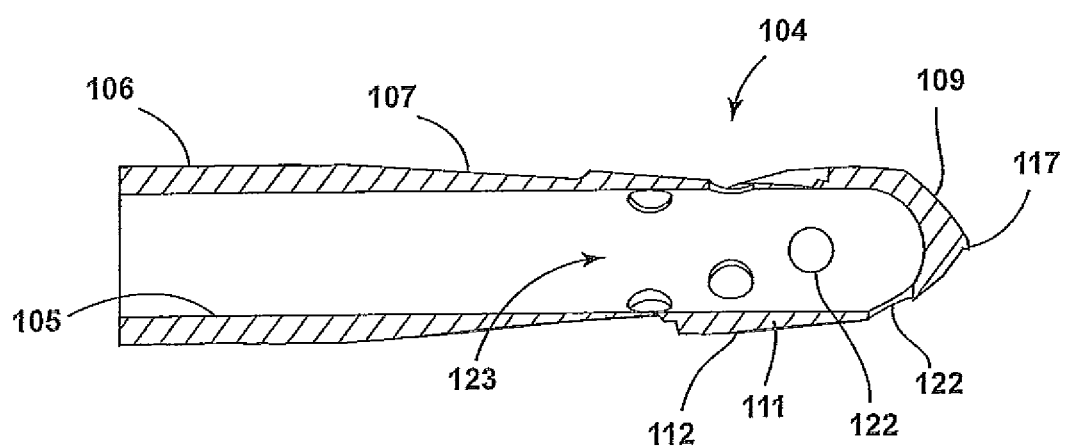
FIG. 8 is a cross-sectional view as seen generally along line VIII-VIII in FIG. 5.
Figure 9:
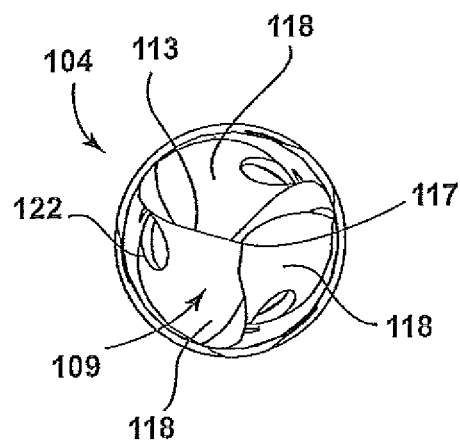
FIG. 9 is a further enlarged distal end view of the first embodiment of the cutting head of the surgical accessory shown in FIGS. 5-8.
Figure 10:
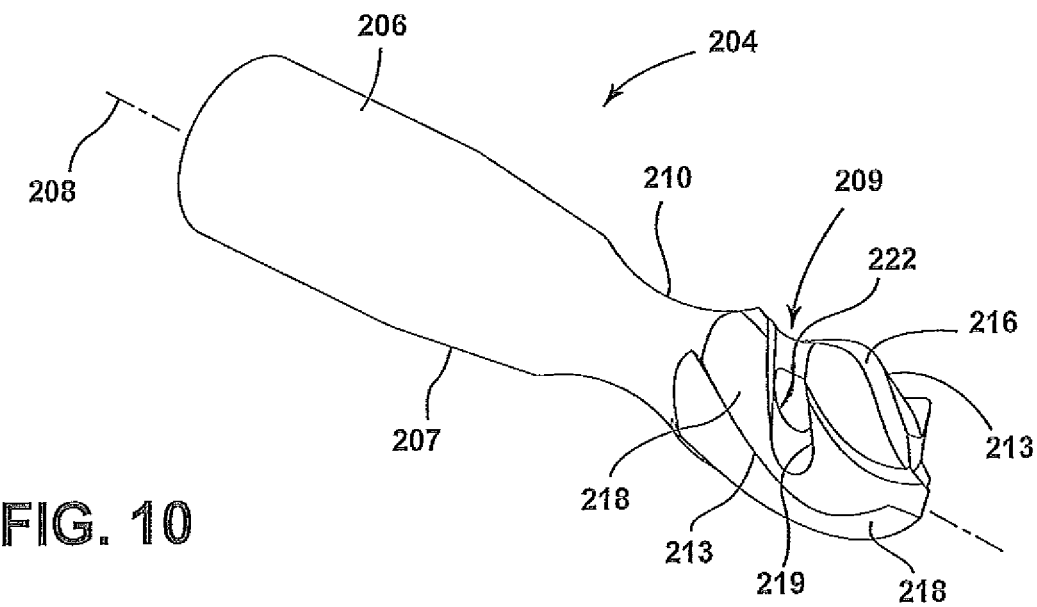
FIG. 10 is an enlarged perspective and isolated view of a second embodiment of the cutting head of the surgical accessory.

The cutting head 104 includes a tubular proximal end 106 of a generally constant diameter, a tubular neck portion 107 extending distally from the proximal end 106 and a distal end 109 which extends distally from the distal end of neck portion 107. As best shown in FIGS. 5-8, the neck portion 107 tapers gradually inwardly towards an axis 108 of the cutting head 104 as the neck portion 107 projects away from the proximal end 106. Distal end 109 is configured for cutting bodily tissue and has a configuration of what is commonly considered a bur. Distal end 109 is defined by a generally cylindrical wall 111 defining an exterior surface 112 extending both circumferentially about and axially along distal end 109 and a plurality of cutting edges 113. Wall 111 is closed at distal end 109, as best shown in FIG. 8. Cutting edges 113 project outwardly from exterior surface 112 in a direction away from the axis 108, and additionally extend in a helical manner about the axis 108 along the longitudinal extent of the distal end 109 and in a generally parallel manner with one another along a majority of the longitudinal extent of the distal end 109. Each cutting edge 113 defines the radially outermost extent of a cutting face 116 formed on the exterior surface 112 of the wall 111. These cutting edges 113 extend gradually towards one another in the proximal to distal direction and terminate adjacent a tip 117 of the distal end 109, as best shown in FIGS. 8 and 9. The wall 111 includes a plurality of wall segments 118, each of which extends circumferentially between a pair of circumferentially adjacent cutting edges 113. Each wall segment 118 thus effectively defines a flute or groove, each of which extends helically about the axis 108 along distal end 109 between a respective pair of cutting edges 113. It will be appreciated that the cutting edges 113 may alternatively be non-helical or substantially straight so as to extend generally parallel with the axis 108 or so as to be oriented at an angle relative to the axis 108. The respective wall segments/flutes 118 in this embodiment would thus also be substantially straight.

Referring again to FIGS. 5-9, the wall 111 of distal end 109 of cutting head 104 defines therein at least one, and in the illustrated embodiment, a plurality, of suction openings 122. One suction opening 122 is disposed in at least one of the wall segments 118, and in the illustrated embodiment a plurality of suction openings 122 are disposed in each wall segment 118. Each suction opening 122 extends completely through the respective wall segment 118 so as to communicate with the hollow interior 105 of cutting head 104. In the illustrated embodiment, the suction openings 122 of each wall segment 118 are oriented in a longitudinal row 123 closely adjacent one of the cutting edges 113. More specifically, the suction openings 122 of each row 123 are formed in the cutting head 104, for example by drilling, so that they follow the helical angle of the respective cutting edge 113 and so that the suction holes 122 lie directly in front of the cutting face 116 of the respective cutting edge 113 when considered the context of the rotational direction of the cutting head 104 during use (as shown by the arrow in FIG. 5).

The cutting head 104 of the illustrated embodiment includes a plurality of rows 123 of suction openings 122, with each row 123 including a plurality of suction openings 122, and a plurality of cutting edges 113 and corresponding cutting faces 116. It will be appreciated that the number of cutting edges 113/cutting faces 116 will vary depending upon the dimensions of the cutting head 104 and/or the type of cutting action desired, and the three cutting edges 113/cutting faces 116 disclosed herein are presented only as an example of one suitable configuration for a cutting head 104. Further, each cutting edge 113/cutting face 116 may have a row 123 of suction openings 122 disposed immediately adjacent thereto as shown herein, or a lesser number of rows 123 may be provided. Additionally, each row 123 may include four suction openings 122 as shown herein, or may include a greater or lesser number of suction openings 122. Still further, it may be suitable to include one suction opening 122 directly adjacent each cutting edge 113/cutting face 116.

The cutting element 33 is assembled to the outer tubular housing element 32 by inserting the distal end 91 of drive shaft 88 of cutting element 33 into bore 41 at the proximal end of hub 34. During this insertion, the enlarged head 86 of hub 80 expands the seal 45 and the head 86 pushes past the stop tabs 58, at which point the seal 45 essentially resumes its original shape. The stop tabs 58, while allowing some axial displacement of cutting element 33 relative to housing element 32, prevent the cutting element 33 from detaching or falling out of the housing element 32 due to gravitational forces.

The assembled accessory 12 is secured to the handpiece 11 in a similar manner to that described in the '559 patent referenced above, and will accordingly be only briefly described here. Accessory 12 is attached to handpiece 11 by inserting the hubs 34 and 80 into the open distal end of collet 26. The ears 37 of hub 34 seat within collet 26, and the locking ring 27 serves to hold the accessory 12 within handpiece 11. The above securement of the accessory 12 to handpiece 11 causes the drive element 81 to engage the motor output shaft 16. More specifically, the drive pin 17 of output shaft 16 seats within slot 84 of drive element 81, such that the rotational movement of output shaft 16 is transferred to the cutting element 33.

In operation, the distal end of tool 10 is inserted into the surgical site. The cutting element 33 is controlled by a control unit (not shown) connected to handpiece cable 18, which control unit supplies electrical power to the motor 15 of handpiece 11 in order to actuate cutting element 33 and control the rotational speed thereof. If cutting of tissue is desired, then motor 15 is activated so as to cause cutting element 33 to rotate within and relative to outer housing element 32. In this regard, it will be appreciated that the control unit may include appropriate control buttons so as to allow the surgeon or operator to select the desired accessory operations. These control functions of the cutting element 33 may alternatively be performed directly from the handpiece 11 which would then include the appropriate control buttons thereon. Alternatively, the control unit may be associated with a switch, either through a suitable cable or wirelessly, to allow the surgeon to operate the controls remotely. Such a switch may be a footswitch or a hand switch.

As shown in FIG. 4, with the cutting element 33 disposed within housing element 32 and the accessory 12 secured to handpiece 11 as described above, the cutting head 104 is positioned adjacent the window 67 of the housing element 32 so that at least a portion of the cutting head 104 is exposed. In this regard, the cutting head 104 is shown herein as being covered one side thereof by the distal end 66 of the housing element 32. However, it will be appreciated that other configurations of the housing element distal end 66 are within the scope of the invention. For example, the housing tube 64 of housing element 32 may be provided with a length which allows full exposure of the cutting head 104 axially beyond the distal end 66 of housing tube 64, so that the cutting head is unhooded or uncovered completely.

If desirable or necessary, suction can be provided at the surgical site by manipulating valve 22 on handpiece 11 to draw surgical debris from the surgical site through the suction openings 122 and into the interior 105 of cutting head 104, into drive shaft suction passage 89, into handpiece suction passage 20 and proximally through the handpiece 11 towards the suction pump. In this regard, the positioning of the suction openings 122 directly in front of the cutting face 116 of the respective cutting edge 113 provides a direct entry port into the interior 105 of cutting head 104. More specifically, when the cutting element 33 is rotating and removing tissue during a surgical procedure and suction is applied, bone or other debris generated by the cutting action of the cutting edges 113 is immediately evacuated from the surgical site via the suction openings 122, into the interior 105 of cutting head 104 and on through the handpiece 11. This placement of the suction openings 122 can thus prevent or at least minimize occlusion of the surgeon's field of view by surgical debris.

Further, the size and/or number of the suction opening or openings according to the invention are chosen in relation to the size and/or configuration of the cutting features provided on cutting head 104. More specifically, some cutting features will cause the severing of larger pieces of tissue, which means that the size of the suction opening or openings should be large enough to allow passage of the severed tissue into the cutting head 104. Likewise, some cutting features will result in the severing of smaller pieces of tissue and thus the suction openings can be smaller and/or lesser in number.

Figure 15:
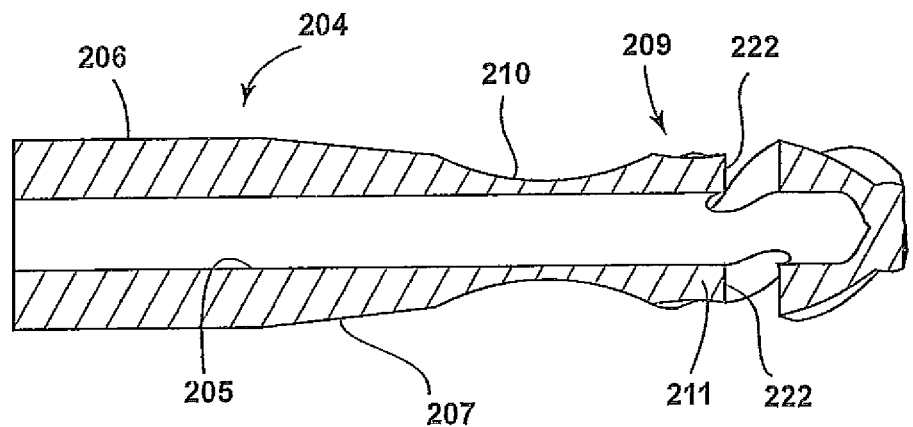
FIG. 15 is a cross-sectional view as seen generally along line XV-XV in FIG. 13.
Figure 16:
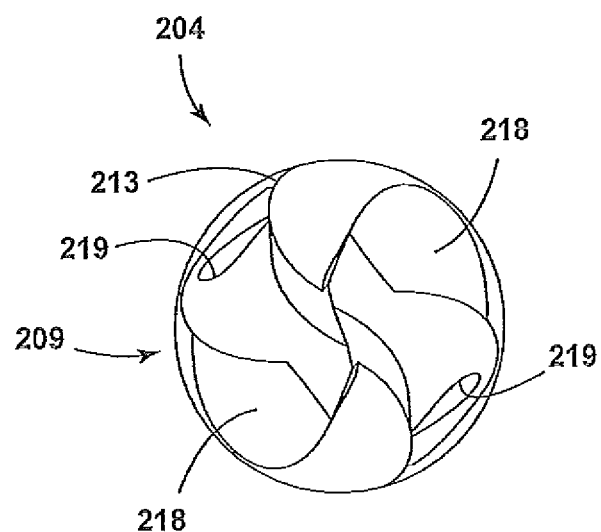
FIG. 16 is a further enlarged distal end view of the second embodiment of the cutting head of the surgical accessory shown in FIGS. 10-15.
Figure 17:
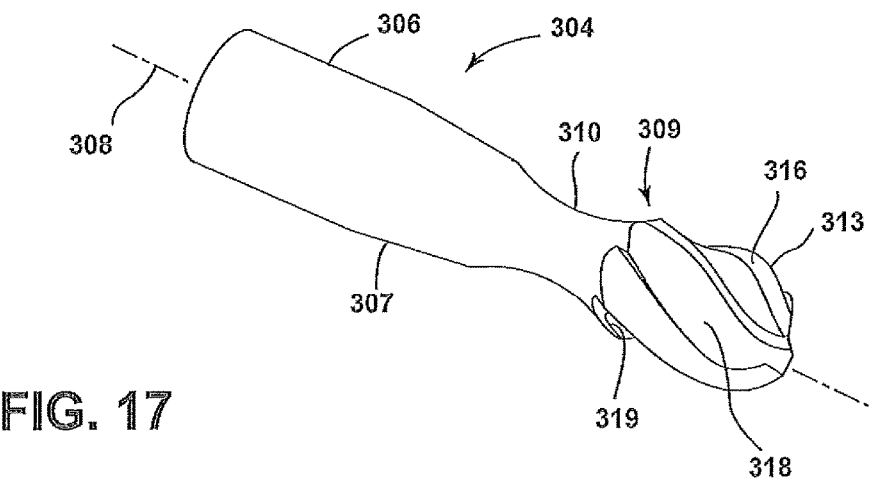
FIG. 17 is an enlarged perspective and isolated view of a third embodiment of the cutting head of the surgical accessory.
Figure 18:
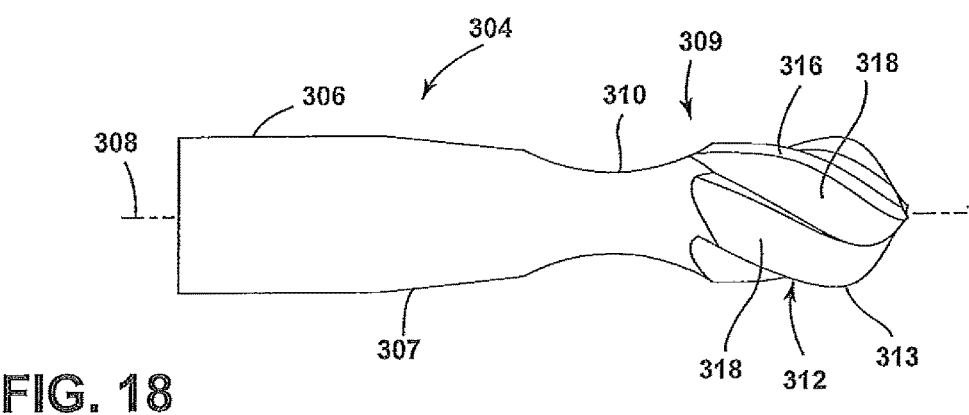
FIG. 18 is an enlarged and isolated side view of the third embodiment of the cutting head of the surgical accessory.
Figure 19:
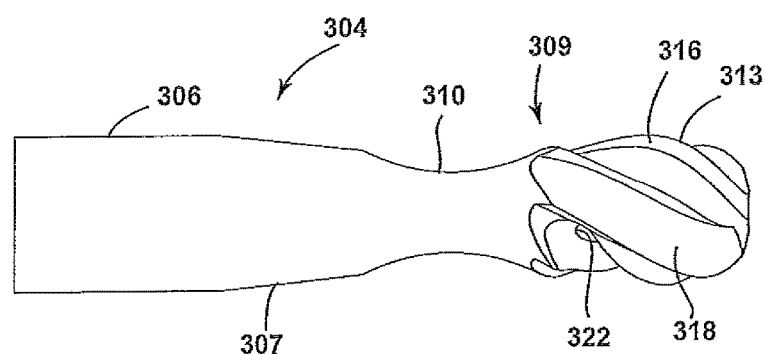
FIG. 19 is an enlarged and isolated side view of the third embodiment of the cutting head of the surgical accessory rotated approximately 90 degrees away from the viewer from the position shown in FIG. 18.
Figure 20:
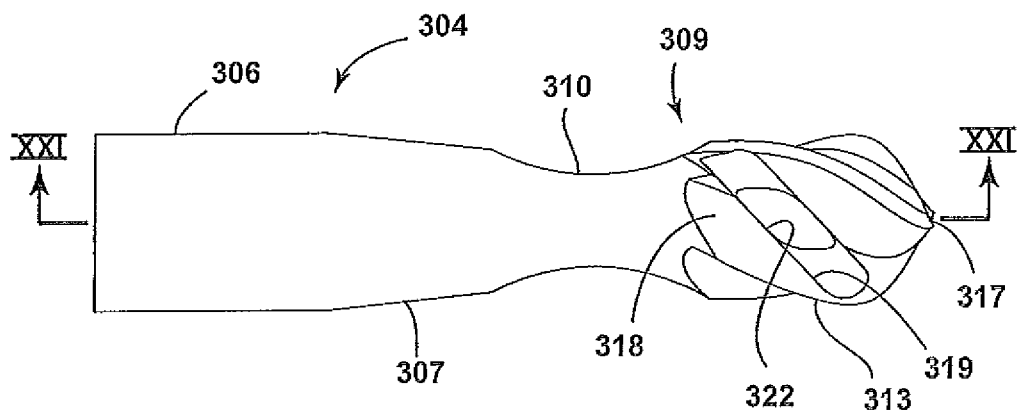
FIG. 20 is an enlarged and isolated side view of the third embodiment of the cutting head of the surgical accessory rotated approximately 180 degrees from the position shown in FIG. 18.
Figure 21:
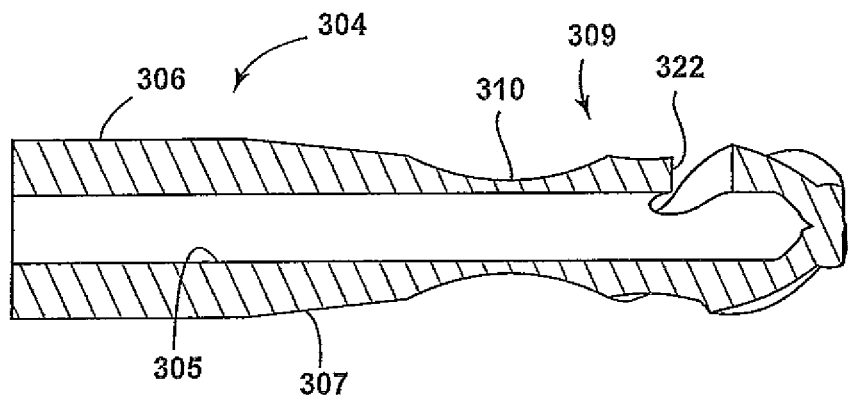
FIG. 21 is a cross-sectional view as seen generally along line XXI-XXI in FIG. 20.
Figure 22:
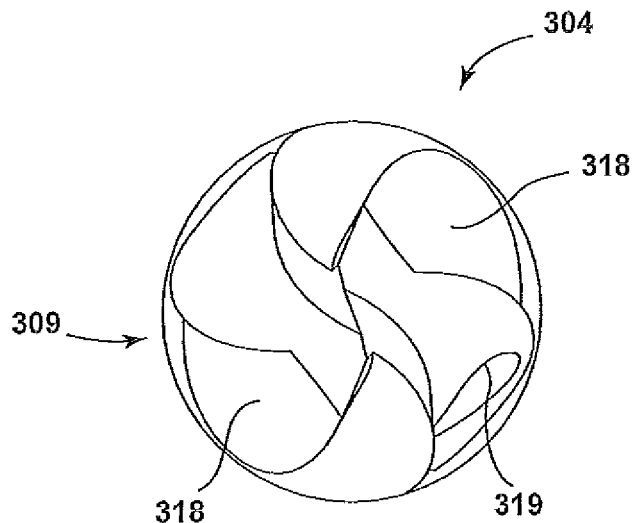
FIG. 22 is a further enlarged distal end view of the third embodiment of the cutting head of the surgical accessory shown in FIGS. 17-21.
Figure 23:
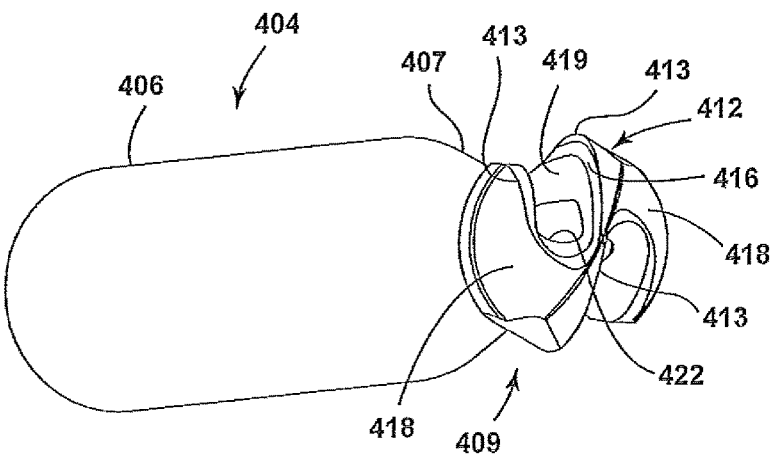
FIG. 23 is an enlarged perspective and isolated view of a fourth embodiment of the cutting head of the surgical accessory.
Figure 24:
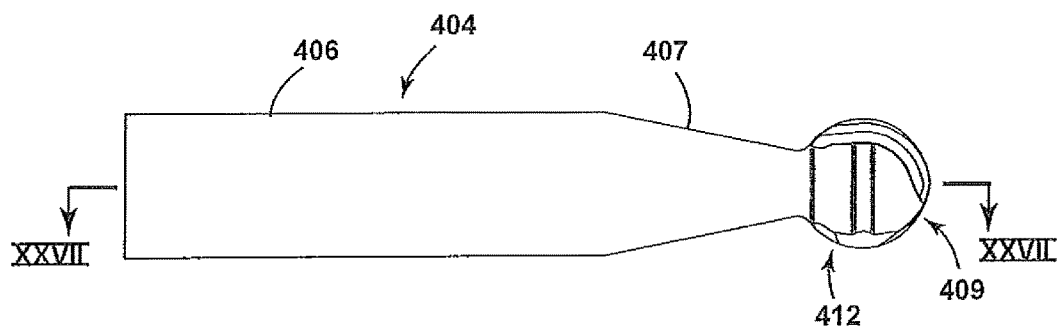
FIG. 24 is an enlarged and isolated side view of the fourth embodiment of the cutting head of the surgical accessory.
Figure 25:
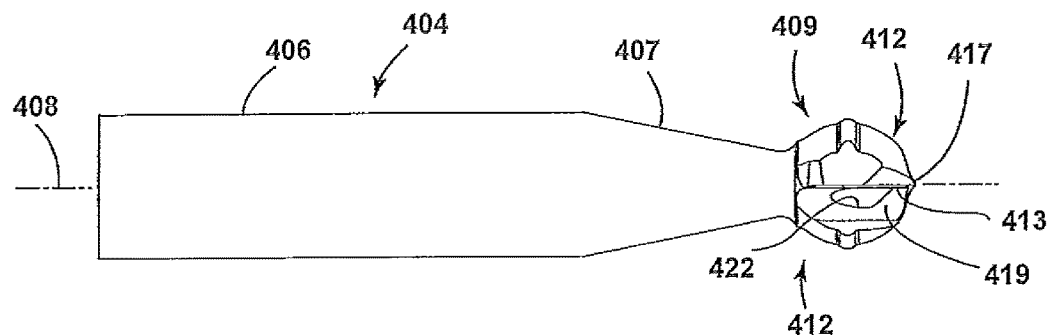
FIG. 25 is an enlarged and isolated side view of the fourth embodiment of the cutting head of the surgical accessory rotated approximately 90 degrees away from the viewer from the position shown in FIG. 24.
Figure 26:
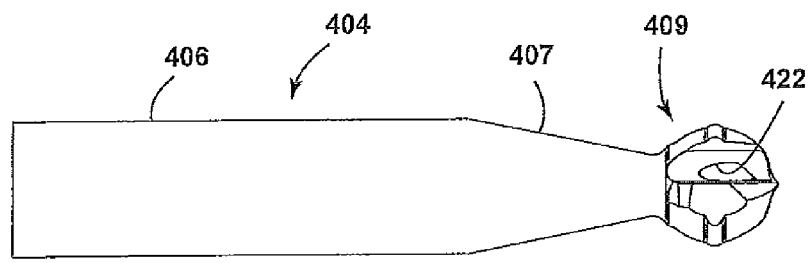
FIG. 26 is an enlarged and isolated side view of the fourth embodiment of the cutting head of the surgical accessory rotated approximately 180 degrees from the position shown in FIG. 25.

FIGS. 10-16 illustrate a second embodiment of the invention which will now be described. Components of the second embodiment which are similar or identical to components of the first embodiment will include the same reference numbers as in the prior embodiment plus "100", and a detailed description of all components will accordingly not be provided. The cutting head 204 according to the second embodiment is generally cylindrical and tubular, and defines a hollow interior 205 which extends along substantially the entire longitudinal extent of the cutting head 204. The cutting head 204 includes a tubular proximal end 206 of a generally constant diameter, a tubular neck portion 207 extending distally from the proximal end 206 and a distal end 209 which extends distally from the distal end of neck portion 207. The neck portion 207 tapers gradually inwardly towards an axis 208 of the cutting head 204 as the neck portion 207 projects away from the proximal end 206. Distal end 209 is configured for cutting bodily tissue and is defined by a generally cylindrical wall 211 defining an exterior surface 212 extending both circumferentially about and axially along distal end 209, and a plurality of cutting edges 213. Wall 211 is closed at the distal end 209, as best shown in FIGS. 15 and 16. The cutting edges 213 project outwardly from exterior surface 212 in a direction away from the axis 208, and additionally extend in a helical manner about the axis 208 along the longitudinal extent of the distal end 209 and in a generally parallel manner with one another along a majority of the longitudinal extent of the distal end 209. Each cutting edge 213 defines the radially outermost extent of a corresponding cutting face 216 formed on the exterior surface 212 of the wall 211. These cutting edges 213 extend gradually towards one another in the proximal to distal direction and terminate adjacent a tip 217 located on the distal end 209. The wall 211 includes a plurality of wall segments 218, each of which is positioned circumferentially between a pair of circumferentially adjacent cutting edges 213. Each wall segment 218 thus effectively defines a flute or groove, each of which extends helically about the axis 208 along distal end 209 between a respective pair of cutting edges 213.

Figure 11:
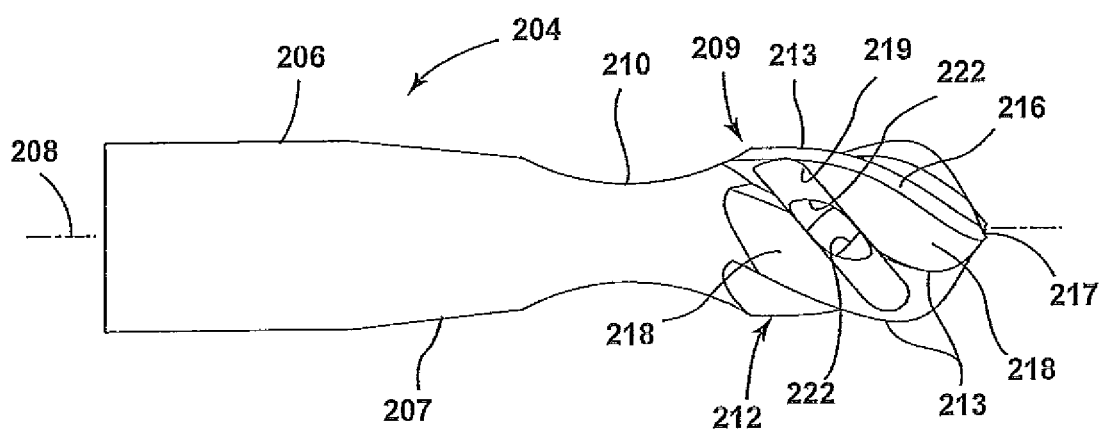
FIG. 11 is an enlarged and isolated side view of the second embodiment of the cutting head of the surgical accessory.

The cutting head 204 of the second embodiment includes a pair of suction openings 222 located on opposite sides of the distal end 209 of the cutting head 204. One method of forming the suction openings 222 is to cut an elongated groove or grooved area 219 into the material of the distal end 209 of the cutting head 204 separately from the cutting process for forming the grooves or flutes 218 of the cutting head 204. In this regard, the grooved area 219 can, in one embodiment, be formed prior to the grooves/flutes 218. The grooved areas 219 are formed on opposite sides of the cutting head 204 and are oriented transversely relative to one another. This cutting process results in elongated or generally elliptically-shaped suction openings 222 located at the bottom of each grooved area 219. In the illustrated embodiment and as best shown in FIG. 11, each grooved area 219 and thus each corresponding suction opening 222 is oriented transverse to the axis 208 of the cutting head 204, and transverse to a cutting edge 213. The suction openings 222 thus interrupt the corresponding cutting edge 213. However, given that there is some overlap between an end of one cutting edge 213 and the beginning of the adjacent or next cutting edge 213, a smooth-cut finish can be achieved even with this interruption.

Figure 12:
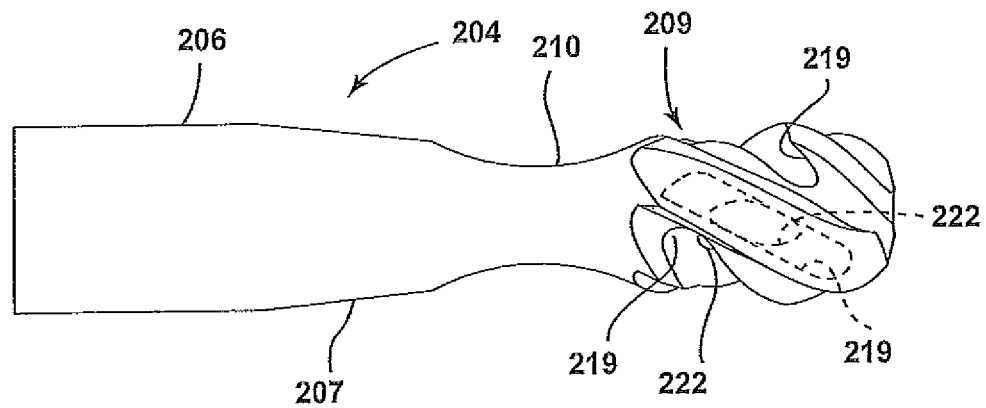
FIG. 12 is an enlarged and isolated side view of the second embodiment of the cutting head of the surgical accessory rotated approximately 90 degrees away from the viewer from the position shown in FIG. 11.
Figure 13:
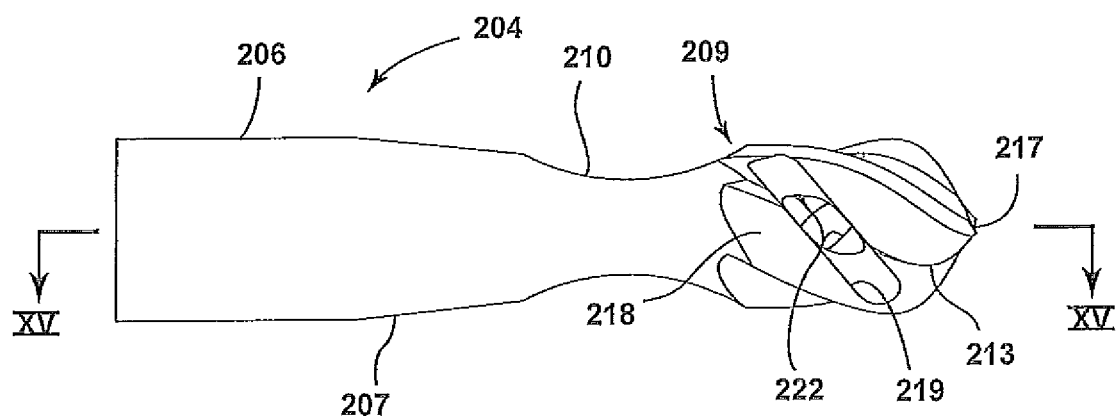
FIG. 13 is an enlarged and isolated side view of the second embodiment of the cutting head of the surgical accessory rotated approximately 180 degrees from the position shown in FIG. 11.
Figure 14:
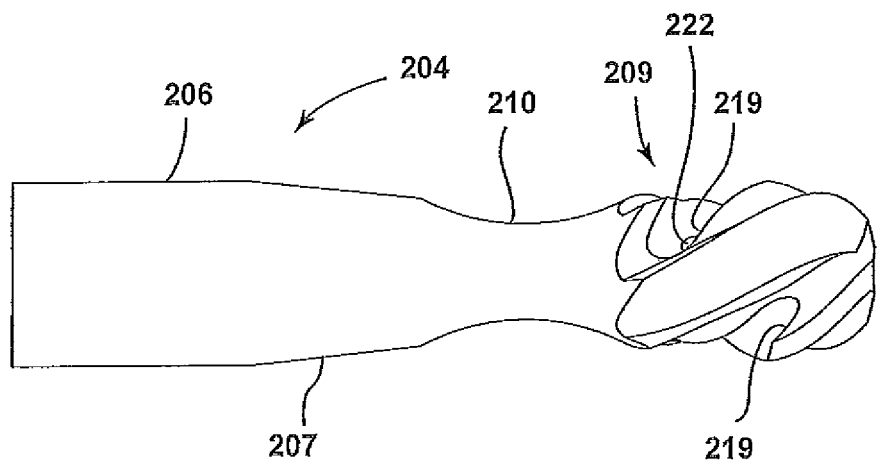
FIG. 14 is an enlarged and isolated side view of the second embodiment of the cutting head of the surgical accessory rotated approximately 180 degrees away from the viewer from the position shown in FIG. 12.

The suction openings 222 need not be provided in directions transverse to the respective cutting edges 213 as described above, and instead may be provided within the respective wall segments 218, as shown in dotted lines in FIG. 12. In other words, the suction openings 222 can be aligned with or primarily located in the wall segments/flutes 218.

Each suction opening 222 extends completely through the respective wall 211 so as to communicate with the hollow interior 205 of the cutting head 204. In the illustrated embodiment, the suction openings 222 traverse the respective cutting edge 213, and thus are located directly where tissue is being excised. In the alternative embodiment illustrated in dotted lines in FIG. 12 as discussed above, the suction opening or openings 222 lie directly in front of the cutting face 216 of the respective cutting edge 213 when considered the context of the rotational direction of the cutting head 204 during use. This orientation of the suction openings 222 provides a direct entry port into the interior 205 of the cutting head 204 so that bone or other debris generated by the cutting action of the cutting edges 213 is immediately evacuated from the surgical site via the suction openings 222. Further, by forming the suction openings 222 and the grooves/flutes 218 in separate cutting or process steps as discussed above, the orientation and/or the size of the respective suction openings 222 can be modified without modifying the configuration and/or trajectory of the cutting edges 213.

FIGS. 17-22 illustrate a third embodiment of the invention. Components of this third embodiment which are similar or identical to components of the first embodiment will include the same reference numbers as in the prior embodiment plus "200". The primary difference between the third embodiment as shown in FIGS. 17-22 and the second embodiment discussed above is that a single suction opening 322 is provided as compared to the two suction openings 222 included in the second embodiment. In this regard, the cutting head 304 includes a suction opening 322 located on one side of the distal end 309 thereof. In the illustrated embodiment, the suction opening 322 is formed by cutting an elongated groove or grooved area 319 into the material of the distal end 309 of the cutting head 204 separately from the cutting process or step which forms the grooves or flutes 318 of the cutting head 304. As is the case with the second embodiment, the grooved area 319 is oriented transversely relative to the axis 308 of the cutting head 304, and transverse to a cutting edge 313. The suction opening 322 thus interrupts the corresponding cutting edge 313. As discussed above, it will be appreciated that the suction opening can alternatively be provided primarily within the respective wall segments/flutes 318, as shown in dotted lines in FIG. 12.

FIGS. 23-29 illustrate a fourth embodiment of the invention. Components of this fourth embodiment which are similar or identical to components of the first embodiment will include the same reference numbers as in the prior embodiment plus "300". The cutting head 404 according to the fourth embodiment is generally cylindrical and tubular, and defines a hollow interior 405 which extends along substantially the entire longitudinal extent of the cutting head 404. The cutting head 404 includes a tubular proximal end 406 of a generally constant diameter, a tubular neck portion 407 extending distally from the proximal end 406 and a spherical distal end 409 which extends distally from the distal end of neck portion 407. Distal end 409 is configured for cutting bodily tissue and is defined by a generally cylindrical and spherical wall 411 defining an exterior surface 412 extending both circumferentially about and axially along the distal end 409, and a plurality of cutting edges 413. The cutting edges 413 project outwardly from exterior surface 412 in a direction away from the axis 408, and additionally extend in a generally linear manner in the proximal to distal direction along the longitudinal extent of the distal end 409 and in a generally parallel manner with one another along a majority of the longitudinal extent of the distal end 409. Each cutting edge 413 defines the radially outermost extent of a corresponding cutting face 416 formed on the exterior surface 412 of the wall 411. These cutting edges 413 extend gradually towards one another in a proximal to distal direction and terminate adjacent a tip 417 of the distal end 409. The wall 411 includes a plurality of wall segments 418, each of which is positioned circumferentially between the cutting edges 413.

Figure 27:
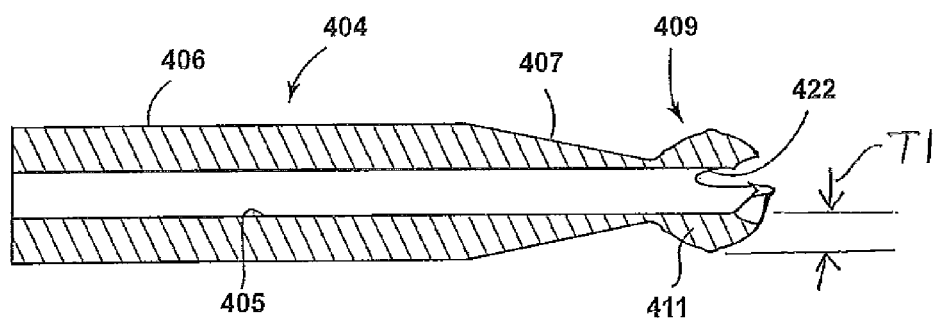
FIG. 27 is a cross-sectional view as seen generally along line XXVII-XXVII in FIG. 24.
Figure 28:
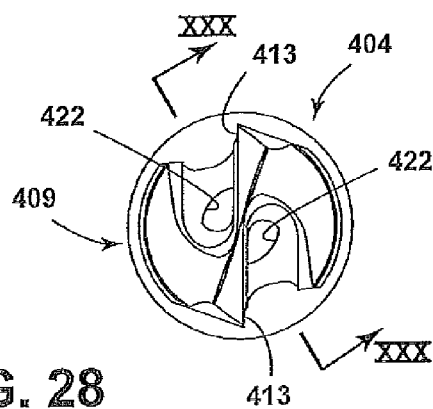
FIG. 28 is a further enlarged distal end view of the fourth embodiment of the cutting head of the surgical accessory shown in FIGS. 23-27.
Figure 29:
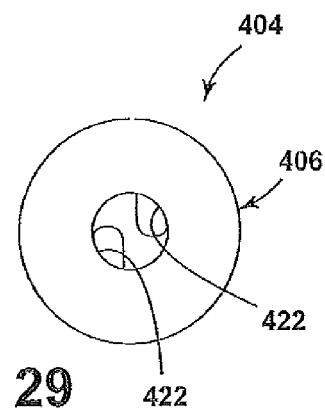
FIG. 29 is a further enlarged proximal end view of the fourth embodiment of the cutting head of the surgical accessory shown in FIGS. 23-27.
Figure 30:
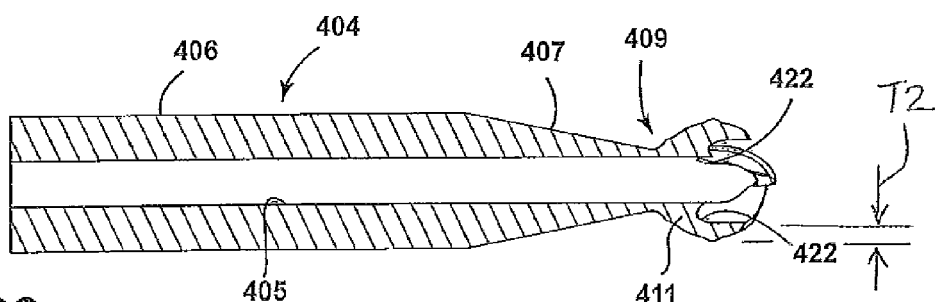
FIG. 30 is a cross-sectional view of the fourth embodiment of the cutting head of the surgical accessory as seen generally along line XXX-XXX in FIG. 27.

The cutting head 404 includes a pair of suction openings 422 located on opposite sides of the distal end 409 of the cutting head 404. One method of forming the suction openings 422 is to cut an elongated groove or grooved area 419 into the wall 411, and specifically into portions of the respective wall segments 418, of the cutting head 404. These grooved areas 419 are formed on opposite sides of the cutting head 404, and form the grooves or flutes of the cutting head 404. The grooved areas 419 extend generally linearly along the cutting head 404 in the proximal to distal direction, and each grooved area 419 is located between the respective cutting edges 413. This cutting process results in elongated or generally elliptically-shaped suction openings 422 located at the bottom of each grooved area 419. In the illustrated embodiment, each suction opening 422 is disposed closely adjacent a respective cutting edge 413. Further, as shown in FIGS. 27 and 30, the wall 411 has a thickness dimension T1, measured in a direction transverse to the axis 408, at an area circumferentially between the suction openings 422 which is substantially greater than a thickness dimension T2 of the wall 411 adjacent the suction openings 422. This increased wall thickness T1 provides the cutting head 404 with increased structural integrity.

It will be appreciated that the cutting head 404 may alternatively be provided with a plurality of suction openings 422 oriented in a longitudinally or axially spaced-apart manner with one another along the cutting head 404 on one or multiple sides thereof between two circumferentially adjacent cutting edges 413, as opposed to a single suction opening 422 located on each side of the cutting head 404 as shown in FIGS. 23-29. That is, the cutting head can have substantially straight cutting edges as shown in FIGS. 23-29, but instead include a row of suction openings as shown in the embodiment of FIGS. 1-9 on one or multiple sides thereof.

Each suction opening 422 extends completely through the wall 411 so as to communicate with the hollow interior 405 of the cutting head 404, and opens both sidewardly and distally through the cutting head 404. In the illustrated embodiment, the suction openings 422 lie directly in front of the cutting face 416 of the respective cutting edge 413 when considered in the context of the rotational direction of the cutting head 404 during use. This orientation of the suction openings 422 provides a direct entry port into the interior 405 of the cutting head 404 so that debris generated by the cutting action of the cutting edges 413 is immediately evacuated from the surgical site via the suction openings 422.

Although particular preferred embodiments of the invention are disclosed in detail for illustrative purposes, it will be recognized that variations or modifications of the disclosed apparatus, including the rearrangement of parts, lie within the scope of the present invention.

What is claimed is:

1. A surgical cutting accessory configured for attachment to a surgical handpiece, said accessory comprising a cutting element defining a suction conduit therein and having a proximal end and a distal end spaced from said proximal end, said distal end defining an axis of rotation and including a plurality of cutting edges extending helically about the axis, said distal end including a first opening therein in communication with said suction conduit and having a portion disposed in a first one of said cutting edges so as to interrupt said first cutting edge, said distal end including a second opening therein in communication with said suction conduit, said second opening having a portion disposed in a second one of said cutting edges so as to interrupt said second cutting edge, said first and second openings being disposed in a substantially diametrically opposed manner with one another on said distal end.

2. The surgical cutting accessory of claim 1, wherein said cutting element includes a hub defining said proximal end thereof and configured for cooperation with a drive member of a powered surgical handpiece, and an elongate drive shaft defining said suction conduit therein and having a proximal end connected to said hub.

3. The surgical cutting accessory of claim 2, wherein said first and second openings each open sidewardly in a direction generally perpendicular to the axis.

4. The surgical cutting accessory of claim 1, wherein said distal end includes a generally cylindrical wall defining said suction conduit, said wall having an exterior surface including said plurality of cutting edges, said cutting edges projecting outwardly from said exterior surface and extending generally helically about the axis, said wall including a plurality of wall segments each extending between and interconnecting a pair of adjacent said cutting edges, said first and second openings each extending transversely across and interrupting the respective said first and second cutting edges so as to extend between two adjacent ones of said wall segments respectively disposed on opposite sides of the corresponding said first or second cutting edge.

5. The surgical cutting accessory of claim 1, wherein said first and second openings each have an opening dimension substantially less than a longitudinal dimension of the corresponding said first or second cutting edge.

6. The surgical cutting accessory of claim 1, wherein each said first and second opening is elongated and said portion thereof extends transversely across the corresponding said first or second cutting edge.

7. The surgical cutting accessory of claim 1, wherein said distal end includes a wall having an inner surface defining said suction conduit and an outer surface facing away from said inner surface, said plurality of cutting edges projecting outwardly from said outer surface, said wall including a plurality of wall segments each forming a flute between a pair of adjacent said cutting edges, each said flute opening radially outwardly with respect to the axis of said distal end, said distal end defining therein first and second elongated grooves extending transversely across the respective said first and second cutting edges so as to interrupt same and opening radially outwardly with respect to the axis of said distal end, said first and second openings each being disposed in a radially innermost region of the respective said first and second grooves and opening into said suction conduit for communication therewith.

8. The surgical cutting accessory of claim 7, wherein said first and second openings are each elongated in shape and each said first and second groove has a longitudinal dimension greater than a longitudinal dimension of the corresponding said first or second opening.

9. A surgical cutting accessory for attachment to a surgical handpiece, said accessory comprising an elongate drive shaft having a proximal end configured for cooperation with a drive member of a powered surgical handpiece and a distal end defining a cutting head thereon, said cutting head defining a longitudinal axis and including a generally cylindrical wall having an exterior surface and defining a hollow interior in communication with a source of suction, and a plurality of cutting edges disposed on said exterior surface and extending generally helically about the axis, said wall including a plurality of wall portions each extending between and interconnecting a pair of adjacent said cutting edges, said cutting head defining therein a pair of suction openings in communication with said interior, a first one of said suction openings having a portion disposed in a first one of said cutting edges so as to interrupt said first cutting edge, and a second one of said suction openings having a portion disposed in a second one of said cutting edges so as to interrupt said second cutting edge, said first and second suction openings being circumferentially spaced from one another on opposite sides of said cutting head.

10. The surgical cutting accessory of claim 9, wherein said first and second suction openings extend transversely across and radially through the respective said first and second cutting edges and open into said suction conduit for communication therewith.

11. A surgical tool comprising a cutting element having a proximal end configured for attachment to a surgical handpiece and a distal end spaced from said proximal end and defining an axis, said distal end having a wall with an inner surface defining a suction conduit extending through a portion of said distal end and an outer surface facing away from said inner surface, said distal end including a plurality of cutting features extending helically about the axis and projecting radially outwardly from said outer surface in a direction away from the axis, said distal end including a first opening extending transversely across a first one of said cutting features such that said first cutting feature is discontinuous, said first opening extending radially through said first cutting feature and opening into said suction conduit for communication therewith, said distal end including a second opening extending transversely across a second one of said cutting features such that said second cutting feature is discontinuous, said second opening extending radially through said second cutting feature and opening into said suction conduit for communication therewith, said first and second openings being disposed substantially diametrically opposite one another along said distal end.

12. The surgical tool of claim 11, wherein said wall includes a plurality of wall sections each extending circumferentially between a pair of adjacent ones of said cutting features and forming a flute therebetween, each said flute opening radially outwardly with respect to the axis of said distal end, each said first and second opening extending transversely across the corresponding said first or second cutting feature and extending between two circumferentially adjacent ones of said wall segments respectively disposed on opposite sides of the corresponding said first or second cutting feature.

13. The surgical tool of claim 11, further including an outer housing assembly having a hub defining a proximal end thereof and configured for cooperation with a coupling arrangement of a powered surgical handpiece, an elongate and generally tubular housing element having a proximal end connected to said hub and an open distal end, said cutting element including an elongate drive shaft disposed within said housing element for movement relative thereto, said proximal and distal ends of said cutting element being disposed at respective opposite ends of said drive shaft, said drive shaft defining a hollow interior in communication with said suction conduit and said first and second openings, and said proximal end of said cutting element being configured for cooperation with a drive member of a powered surgical handpiece.

14. A surgical cutting accessory configured for attachment to a surgical handpiece, said accessory comprising a cutting element defining a suction conduit therein and having a proximal end and a distal end spaced from said proximal end, said distal end defining an axis and including a plurality of cutting edges extending helically about the axis, said distal end including an opening therein in communication with said suction conduit and having a portion disposed in one of said cutting edges so as to interrupt said one cutting edge, said distal end including a wall having an inner surface defining said suction conduit and an outer surface facing away from said inner surface, said plurality of cutting edges projecting outwardly from said outer surface, said wall including a plurality of wall segments each forming a flute between a pair of adjacent said cutting edges, each said flute opening radially outwardly with respect to the axis of said distal end, said distal end defining therein an elongated groove extending transversely across said one cutting edge so as to interrupt said one cutting edge and said groove opening radially outwardly with respect to the axis of said distal end, said opening being disposed in a radially innermost region of said groove and opening into said suction conduit for communication therewith.

* * * * *